(12) United States Patent
Vogt et al.

(10) Patent No.: US 8,662,736 B2
(45) Date of Patent: Mar. 4, 2014

(54) BONE CEMENT SYSTEM

(75) Inventors: Sebastian Vogt, Erfurt (DE); Rochus Stöckli, Buochs (CH); Hubert Büchner, Nürnberg (DE)

(73) Assignee: Heraeus Medical GmbH, Wehrheim (DE)

( * ) Notice: Subject to any disclaimer, the term of this patent is extended or adjusted under 35 U.S.C. 154(b) by 684 days.

(21) Appl. No.: 12/845,885

(22) Filed: Jul. 29, 2010

(65) Prior Publication Data
US 2012/0026825 A1 Feb. 2, 2012

(51) Int. Cl.
*B01F 13/06* (2006.01)

(52) U.S. Cl.
USPC ............. 366/139; 366/163.1; 366/183.2

(58) Field of Classification Search
USPC ............ 366/139, 163.1, 183.1–183.4
See application file for complete search history.

(56) References Cited

U.S. PATENT DOCUMENTS

| | | | |
|---|---|---|---|
| 6,709,149 B1 | 3/2004 | Tepic | |
| 6,755,563 B2 | 6/2004 | Wahlig et al. | |
| 7,073,936 B1 * | 7/2006 | Jonsson | 366/139 |
| 2009/0057168 A1 | 3/2009 | Smit | |
| 2010/0091606 A1 * | 4/2010 | Kwan et al. | 366/139 |
| 2011/0273954 A1 * | 11/2011 | Greter et al. | 366/142 |

FOREIGN PATENT DOCUMENTS

| | | |
|---|---|---|
| DE | 19532015 A1 | 3/1997 |
| DE | 200 08 103 U1 | 9/2001 |
| DE | 698 12 726 T2 | 2/2004 |
| EP | 1005900 A2 | 6/2000 |
| WO | 94/26403 A1 | 11/1994 |
| WO | 0035506 A1 | 6/2000 |
| WO | 2005018830 A2 | 3/2005 |

OTHER PUBLICATIONS

Office Action Issued Feb. 12, 2010 in German Appln. Ser. No. 10 2009 035 067.5.
John Charnley, "Anchorage of the Femoral Head Prosthesis to the Shaft of the Femur", The Journal of Bone and Joint Surgery, vol. 42B, No. 1, pp. 28-30, (1960).
S. J. Breusch et al., "Der Stand der Zementiertechnek bei Huefttotalendoprothesen in Deutschland", Z. Orthop., vol. 137, pp. 101-107, (1999).
EP Search Report issued Dec. 6, 2010 in EP Application No. 10007817; Written Opinion.

* cited by examiner

*Primary Examiner* — David Sorkin
(74) *Attorney, Agent, or Firm* — Panitch Schwarze Belisario & Nadel LLP

(57) ABSTRACT

A bone cement system (100) is provided having a mixing facility (10) for mixing and dispensing of bone cement, a reservoir container (112) for a monomer, and a conveyor (122). The mixing facility (10) has a mixing cylinder (20), which stores a bone cement powder. The monomer can be conveyed from the reservoir container (112) into the mixing cylinder (20) by the conveyor (122). A sieve element is (4) is arranged between the reservoir container (112) and the mixing facility (10), in order to prevent ingress of the bone cement powder from the mixing cylinder (20) into the conveyor (122). The mixing device (10) included a dispensing opening (23) for dispensing a bone cement mixed from the bone cement powder and the monomer. The dispensing opening (23) includes a shield (1) having at least one through-opening (2). The ratio of the area of the through-opening (2) to the area of the sieve element (4) is at least 1 to 3, and the distance between the shield (1) and the sieve element (4) is at least 1 mm.

11 Claims, 3 Drawing Sheets

BONE CEMENT SYSTEM

BACKGROUND OF THE INVENTION

The invention relates to a bone cement system having a mixing facility for the mixing and dispensing of bone cement, a reservoir container for a monomer, and a conveyor, wherein the mixing facility comprises a mixing cylinder, the mixing cylinder stores a bone cement powder, the monomer can be conveyed from the reservoir container into the mixing cylinder by the conveyor, a sieve element is arranged between the reservoir container and the mixing facility to prevent the ingress of the bone cement powder from the mixing cylinder into the conveyor, and the mixing facility comprises a dispensing opening for dispensing a bone cement obtained by mixing the bone cement powder and the monomer.

PMMA bone cements have been known for decades and are based on the groundbreaking work of Sir Charnley (Charnley, J., "Anchorage of the femoral head prosthesis of the shaft of the femur," *J. Bone Joint Surg.* 42: 28-30 (1960)). The basic structure of PMMA bone cements has remained the same ever since. PMMA bone cements includes a liquid monomer component and a powder component. The monomer component generally contains the monomer, methylmethacrylate, and an activator (N,N-dimethyl-p-toluidine) dissolved therein. The powder component comprises one or more polymers made by polymerization, preferably suspension polymerization, based on methylmethacrylate and co-monomers, such as styrene, methylacrylate or similar monomers, a radio-opaquer, and the initiator, dibenzoylperoxide. When mixing the powder component with the monomer component, swelling of the polymers of the powder component in the methylmethacrylate leads to the formation of a dough that can be shaped plastically. When mixing the powder component with the monomer component, the activator, N,N-dimethyl-p-toluidine, reacts with dibenzoylperoxide while forming radicals. The radicals thus formed trigger the radical polymerization of the methylmethacrylate. Upon advancing polymerization of the methylmethacrylate, the viscosity of the cement dough increases until the cement dough solidifies.

Polymethylmethacrylate bone cements can be mixed in suitable mixing beakers by spatulas by mixing the cement powder with the monomer liquid. This procedure is disadvantageous in that inclusions of air may be present in the cement dough thus formed and may later cause destabilization of the bone cement—also referred to as cement. For this reason, it is preferable to mix bone cement powder with the monomer liquid in vacuum mixing systems, since mixing in a vacuum almost completely removes inclusions of air from the cement dough and thus attains optimal cement quality (Breusch, S. J. et al., "Der Stand der Zementiertechnik bei Hiifttotalendoprothesen in Deutschland" [Current Status of Cemented Total Hip Arthroplasty in Germany], *Z Orthop.*, 137: 101-07 (1999)). Bone cements mixed in a vacuum have substantially lower porosity and thus show improved mechanical properties. A large number of vacuum cementing systems have been disclosed of which the following shall be named for exemplary purposes: U.S. Pat. Nos. 6,033,105, 5,624,184, 4,671,263, 4,973,168, 5,100,241, 5,586,821, and 5,344,232, International Patent Application Publication Nos. WO99/67015 A1 and WO94/26403 A1, European patent application Publication Nos. EP 1 020 167 A2, EP 1 016 452 A2, EP 0 692 229 A1, and EP 1 005 901 A2, and German published patent application No. DE 36 40 279 A1.

A further development is cementing systems in which both the cement powder and the monomer liquid are already packed in separate compartments of the mixing systems and are mixed with each other in the cementing system only right before application of the cement (U.S. Pat. Nos. 5,997,544 and 6,709,149 and EP 0 692 229 A1). A drawback of all of these systems is the transfer of the monomer liquid into the cement powder and the complete mixing of these two components to obtain a homogeneous cement dough which must, in particular, not contain any regions of cement powder that has not been wetted by the monomer liquid. In a mixing system that is currently on the market in Europe, tubes that are arranged on the side of the lower part of the cartridge and penetrate through the cartridge wall are used to introduce the monomer liquid approximately into the middle of the cement powder through the application of a vacuum. There is no mixing facility provided at the tubes that might prevent the ingress of cement powder into the tubes during storage of the mixing system. Clogging of the tubes by cement powder cannot be excluded completely.

Another mixing system for the mixing and dispensing of bone cement is shown in German Patent document DE 698 12 726 T2. This mixing system comprises a mixing cylinder, whereby a sieve element is arranged between the reservoir container and the mixing facility to preventing ress of the bone cement powder from the mixing cylinder into the conveyor. The mixing systems have proven to be disadvantageous in that homogeneous and rapid mixing of the monomer and the bone cement powder cannot be ensured at all times.

Another variant was disclosed in European Patent EP 1 140 234 B1. In this mixing system, the monomer liquid is aspirated through the entire cement powder by a vacuum. The basic approach, i.e., to aspirate the monomer liquid through the entire cement powder in order to achieve optimal mixing and prevent regions of non-wetted cement powder from forming is feasible only if a cement powder is used that swells very slowly after being wetted by the monomer liquid. This means that the high and medium viscosity PMMA bone cements, which currently are most commonly used in endoprosthetics, can be used not at all or with difficulties, since the cement powder of these cements swells immediately after being wetted by the monomer liquid and forms a dough that renders further pervasion of the cement powder by the monomer liquid difficult or even impossible.

BRIEF SUMMARY OF THE INVENTION

It is therefore the object of the invention to develop a bone cement system that is not associated with the aforementioned disadvantages, but is, in particular, protected against clogging by cement powder.

According to the invention, the dispensing opening comprises a shield having at least one through-opening and a ratio of an area of the through-opening to the area of the sieve element is at most 1 to 3, and a distance between the shield and the sieve element is at least 1 mm.

The invention allows the injection of monomer liquid from below into the bone cement powder—also referred to as cement powder—such that the injection system is prevented from becoming sticky, and mixing of the cement powder, as completely as possible, can be achieved. The bone cement system must not get sticky, since this renders complete monomer transfer from the monomer reservoir container into the cement powder impossible. The result of incomplete monomer transfer would be that only a fraction of the intended monomer would form a dough with the cement powder. The resulting dough would therefore be more viscous, and the bone cement—also referred to as cement—would have unpredictably changed mechanical properties after it hardens, as compared to correctly mixed cement that is produced to have a predetermined ratio of monomer liquid to cement powder.

The bone cement system works such that the application of a vacuum opposite from the through-opening generates a negative pressure in the feed opening, and first the residual air present in the system and then the monomer liquid is aspirated into the intervening space. The air arriving first moves through the sieve element and carries along the cement powder present in the intervening space through the through-opening in the direction of the mixing cylinder. As a result, the intervening space no longer contains cement powder and is empty. Subsequently, the monomer liquid is aspirated through the sieve element. Accordingly, the sieve element facilitates the bone cement powder not flowing into the conveyor and clogging the same upon contact with the monomer liquid. Therefore, according to the invention, the sieve element separates the conveyor and the mixing cylinder, such that no bone cement powder can flow into the conveyor.

An advantageous further embodiment of the bone cement system according to the invention is characterized in that the mixing facility comprises a dispensing opening for dispensing a bone cement mixed from the bone cement powder and the monomer. A bone cement forms after mixing of the bone cement powder and the monomer. Before it hardens, the bone cement needs to be dispensed from the bone cement system and, preferably, implanted into the patient. It has proven to be advantageous for this purpose to have a dispensing opening being present, through which the bone cement can be pressed from the mixing cylinder. Advantageously, the dispensing opening is designed to be funnel-shaped.

Another advantageous embodiment is characterized in that the sieve element is stored in an intervening space that can be connected to the dispensing opening of the mixing facility and in which the conveyor ends. Both the dispensing opening of the mixing facility and the conveyor end in the intervening space. Accordingly, the monomer flows from the reservoir container through the intervening space into the mixing cylinder. The sieve element according to the invention is arranged in the intervening space. This embodiment is advantageous in that the sieve element is not arranged in the dispensing opening through which the mixed bone cement is dispensed later on. However, the sieve element prevents the bone cement powder from flowing from the mixing cylinder into the conveyor.

Another advantageous embodiment is characterized in that the sieve element has a mesh size of less than 30 μm, in particular a mesh size between 5 μm and 25 μm. The mesh size ensures, on the one hand, that the bone cement powder cannot flow from the mixing facility into the conveyor. On the other hand, the flow of the monomer, in particular liquid monomer, from the reservoir container into the mixing cylinder is impeded only to a minor degree by the mesh of the sieve element. Accordingly, a sieve element with a mesh size between 30 μm and 5 μm represents a connection element between the reservoir container and the mixing facility that is open only on one side.

In another advantageous embodiment, the dispensing opening comprises a shield with at least one through-opening. Advantageously, the shield is arranged between the mixing facility, in particular the dispensing opening, and the sieve element. In this context, the dispensing opening determines the quantity of monomer that can flow into the mixing cylinder in a unit of time. Advantageously, the area of the through-opening is smaller than the area of the sieve element. Advantageously, the sieve element and the shield are part of the intervening space. Adjacent to the intervening space, there is, on the one hand, the conveyor of the reservoir container and, on the other hand, the dispensing opening of the mixing facility. The intervening space is designed such that it stores, approximately in the middle thereof, the sieve element, which is arranged essentially parallel to the shield. During storage and transport of the polymethylmethacrylate bone cement mixing system, the sieve element prevents penetration of the cement powder in the direction of the feed opening.

The bone cement system works such that the application of a vacuum opposite from the through-opening generates a negative pressure in the feed opening, and first the residual air that is present in the system and then the monomer liquid is aspirated into the intervening space. The air arriving first moves through the sieve element and carries along the cement powder present in the intervening space through the through-opening in the direction of the mixing cylinder. The intervening space then no longer contains cement powder and is empty. Subsequently, the monomer liquid is aspirated through the sieve element. Due to the low mesh size of the sieve element, this causes a marked reduction of the flow rate. To counteract this loss in velocity, the area of the sieve is made correspondingly large. This means that the volume flow is not impeded despite the slower flow rate of the liquid through the sieve element due to the large area thereof. The term, volume flow, is understood to mean the volume of monomer liquid per unit time that emanates from the feed opening. Subsequently, the monomer liquid accumulates in the intervening space and moves in the direction of the through-opening.

The bone cement system according to the invention is characterized in that a ratio of an area of the through-opening to the area of the sieve element is at most 1 to 3, preferably in that the ratio of the area of the through-opening to the area of the sieve element is between 1 to 4 and 1 to 20. The area of the through-opening being small compared to the area of the sieve element accelerates the liquid in the dispensing opening in order for the volume flow to be constant. This means that a jet of monomer liquid is generated that is injected into the cement powder that is situated above the through-opening. The jet of monomer spreads in a funnel shape with increasing distance of travel. Due to the high velocity of the monomer jet, the monomer can pass through the cement powder in a sufficiently short time before the cement powder swells to any significant degree. Bone cement powder particles that have already swelled are displaced by the monomer jet.

Preventing an ingress of bone cement powder from the mixing cylinder into the conveyor is promoted by a distance between the shield and the sieve element being at least 1 mm, preferably by the distance between the shield and the sieve element being between 2 mm to 10 mm. The values specified above have been found, surprisingly in extensive measurements, to be particularly preferred in order to ensure that the monomer entering the mixing cylinder, on the one hand, carries along possible bone cement powder residues from the intervening space into the mixing cylinder, and, on the other hand, does not provide the intervening space too large, such that the amount of bone cement powder residues that is deposited therein is as small as possible.

Depending on the bone cement powder that is used, it has proven to be advantageous for the through-opening to be provided to be circular, oval, star-shaped or slit-shaped, in particular for the shield to extend in a funnel shape. The shapes of the through-opening can control the flow behavior of the monomer into the bone cement powder. In particular star- or slit-shaped through-openings provide for a funnel-shaped spreading of the jet of monomer liquid that enters through the shield into the mixing cylinder. In addition, the shield can extend to be funnel-shaped. In this case, the shield works like a Venturi nozzle and effects additional acceleration of the monomer liquid that flows from the intervening space into the mixing cylinder.

In order to mix the monomer with the bone cement powder as homogeneously as possible, it has proven to be advantageous for a mixing plunger to be arranged in the mixing cylinder, whereby the mixing plunger can be moved axially by an actuation rod that is guided to exit in a sealed manner at a first cylinder end. Advantageously, the first cylinder end is situated opposite from a second cylinder end, whereby the second cylinder end comprises the dispensing opening. Accordingly, the monomer flowing into the mixing cylinder can be pulled even further into the mixing cylinder by the mixing plunger and/or the actuation rod in order to ensure homogeneous mixing of the cement powder and the monomer.

One particularity of the mixing facility according to the invention is that a plunger system can be pushed axially into the mixing cylinder in order to dispense a bone cement that is mixed from the bone cement powder and the binding agent, in particular the monomer, through the dispensing opening. The dispensing opening is situated at a second cylinder end of the mixing plunger. The second cylinder end is situated opposite from the first cylinder end. During dispensation, the plunger system is pushed from the direction of the first cylinder end in the direction of the second cylinder end and, in turn, presses the ready-mixed bone cement through the dispensing opening.

In an advantageous further embodiment, the dispensing opening comprises a connector, in particular a connection thread. The connection thread can be used to screw the mixing cylinder into the bone cement system and/or to connect the mixing cylinder to a hose system via which the ready-made bone cement can be introduced into the bone. An applicator gun into which the mixing cylinder is to be clamped can be used for this activity. For ease of use of the applicator gun, the actuation rod can comprise a predetermined breakage point such that the actuation rod can be broken off at a defined place. For dispensing the ready-mixed bone cement, the actuation rod is pulled in the direction of the plunger system until the mixing plunger touches against the plunger system. The plunger system, including the mixing plunger that touches against it in front of it, can be pressed into the mixing cylinder by then breaking off the actuation rod.

Moreover, it is advantageous for the reservoir to store a reservoir container for the monomer. For production of the bone cement, the monomer must be introduced into the bone cement powder. The bone cement then hardens after a certain period of time. It is therefore obvious that the bone cement cannot be delivered such as to be in the device and ready for dispensation. It is therefore necessary for the bone cement powder and the monomer to be stored separately until shortly before dispensation of the bone cement. It is therefore expedient if the reservoir comprises a reservoir container for the monomer. Glass containers, in particular, that are used as reservoir containers for the binding agent, in particular the monomer, have proven to be easy to disinfect. The reservoir can comprise a valve to control the inflow of the monomer. The valve controls and/or triggers the inflow of the monomer from the reservoir container into the device according to the invention.

An advantageous further embodiment of the bone cement system according to the invention is characterized in that the bone cement system comprises a base, whereby the base stores the mixing facility and the reservoir container. The base therefore serves as a platform both for the mixing facility according to the invention and for the reservoir for the binding agent. The mixing facility according to the invention and the reservoir can be arranged at and/or on the base as a kind of foundation of the bone cement system.

An advantageous embodiment of the bone cement system according to the invention is characterized in that the base comprises a coupling for a non-positive (form-fit) and/or positive (force-fit) connection to the mixing facility, in particular a dispensing opening of the mixing facility. Since the mixing facility according to the invention is also to be used for dispensing the bone cement, it is advantageous for the mixing facility to be reversibly separable from the base. This can be attained by the coupling element according to the invention. The coupling element advantageously is a thread onto which the dispensing opening of the mixing facility can be screwed. This provides a secure connection between the base and the mixing facility.

In another advantageous embodiment, the base can store the conveyor. In this case, the conveyor extends through the base. The intervening space can also be arranged in the base. By the connector, it is feasible to connect the intervening space, and thus the conveyor, to the mixing cylinder. In this context, according to the invention, the sieve element preventing ingress of the bone cement powder from the mixing cylinder into the conveyor is arranged in the intervening space.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings.

DETAILED DESCRIPTION OF THE INVENTION

Figure 1:
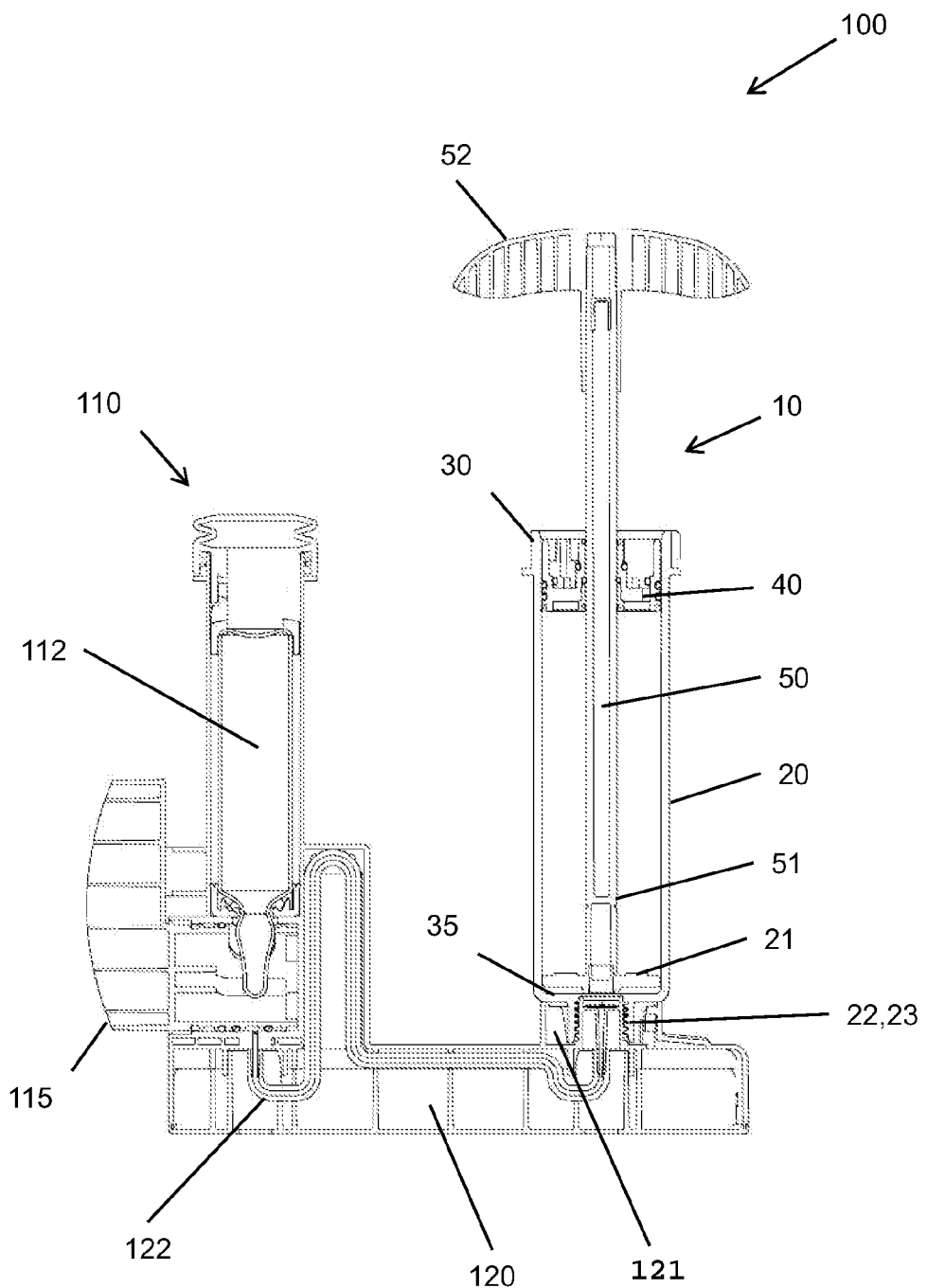
FIG. 1 is a schematic, sectional, elevation view of a bone cement system according to one embodiment of the invention.

FIG. 1 shows a bone cement system 100 according to an embodiment of the invention. The bone cement system 100 comprises a mixing facility 10 for mixing and dispensing bone cement. The mixing facility 10 is stored on a base 120 in the exemplary embodiment shown. The base 120 also carries a reservoir facility 110 for a monomer. The bone cement system 100 serves for mixing the bone cement. For this purpose, bone cement powder is filled into a mixing cylinder 20 of the mixing facility 10. The bone cement powder can subsequently be mixed with the monomer in order to form bone cement. As illustrated in FIG. 1, reservoir facility 110 is part of the bone cement system 100. Reservoir facility 110 stores a reservoir container 112 for the monomer.

An outflow of the monomer from the reservoir container 112 can be controlled and/or triggered via a valve 115. Advantageously, the reservoir container 112 is a glass container that is opened in its head region by the valve 115. The monomer then flows through a conveyor 122 from the reservoir container 112 into the mixing cylinder 20. The transfer flow of the monomer is increased since a negative pressure is present in the mixing cylinder 20. The bone cement powder and the monomer can then be mixed easily and simply by the actuation rod and the mixing plunger 21.

After mixing is completed, the facility 10 can be unscrewed from the base 120. For this purpose, the base 120 comprises a coupling 121 that acts in concert with a connector 22 of the mixing plunger. After separation of the mixing facility 10 from the base 120 is effected, the actuation rod 50 is shifted axially such that the mixing plunger 21 comes to rest against the plunger system 40. Subsequently, the actuation rod can be snapped off at the predetermined breakage point 51. The mixing facility 10 can now be integrated into a cementing gun. Actuation of the cementing gun moves a toothed rack with collar in the direction of the plunger system 40. The plunger system 40 is used for dispensing the bone cement. For this purpose, the plunger system 40 is designed to be axially movable and can be pressed axially into the mixing cylinder 20. This allows the bone cement formed by mixing the bone cement powder and the monomer to be dispensed through a dispensing opening 23.

The prior art knows bone cement systems, in which the monomer liquid is stored in containers on the side of the mixing cylinder. Tubes are used to introduce the monomer liquid approximately in the middle of the cement powder that is arranged in the mixing cylinder. It has proven to be disadvantageous that the arrangement and design of the tubes do not completely exclude clogging of the tubes by cement powder. This can lead to the supplied amount of monomer being insufficient and a non-homogeneous bone cement region may result therefrom.

Figure 2:
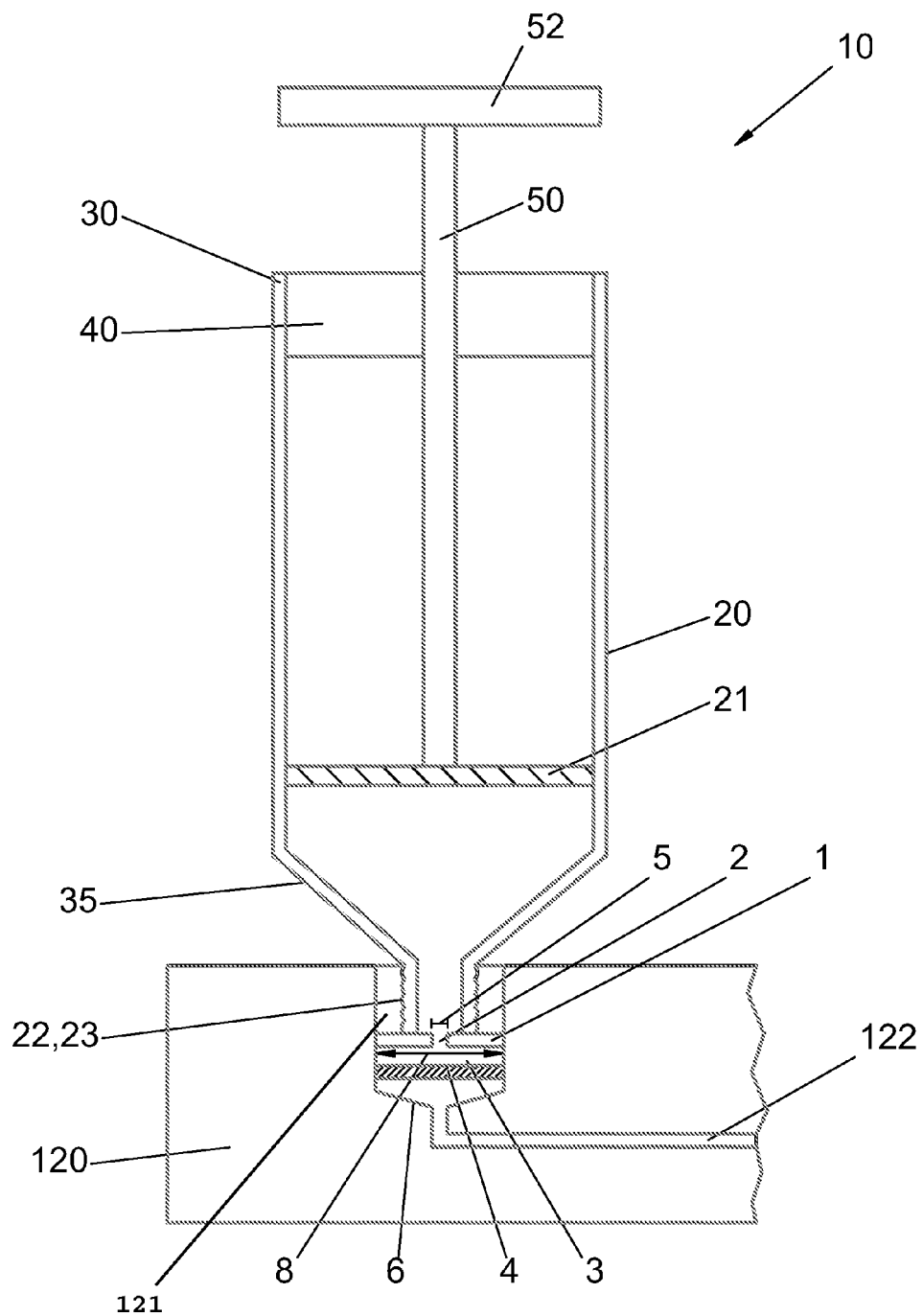
FIG. 2 is a schematic, sectional, elevation view of a mixing facility according to an embodiment of the invention.

In order to overcome this disadvantage, the bone cement system 100 according to an embodiment of the invention comprises a sieve element 4, like the one shown in FIG. 2. FIG. 2 is a sectional drawing analogous to the one in FIG. 1 with the features in the area of the dispensing opening 23 being shown in more detail. As is evident, the base 120 stores the mixing cylinder 20 of the mixing facility 10. The mixing cylinder 20 is connected to the base 120 by a connector 22, a thread in the present case. A shield 1 that comprises at least one through-opening 2 is situated below the dispensing opening 23 in the base. It is evident that the through-opening has a width and therefore an area 5 that is clearly smaller than the area of the sieve element 4 that is arranged underneath. The width thereof is indicated by reference number 8. Advantageously, the area of the through-opening is ¼ to ¹⁄₂₀ of the area of the sieve element 4. The sieve element 4 prevents bone cement from the mixing cylinder 20 from penetrating into and clogging the conveyor 122 during storage and transport.

When the finished bone cement is to be mixed, the bone cement system is connected to a vacuum source (not shown). This generates a negative pressure in the mixing cylinder 20 and in an intervening space 3 that stores the sieve element 4. The negative pressure aspirates residual air from the intervening space 3 in the direction of the vacuum connection, which is generally arranged in the area of a first cylinder end 30. The first cylinder end 30 is opposite the second cylinder end 35, where the dispensing opening 23 is located. The aspiration of the residual air causes any cement powder that is still present in the intervening space 3 to be aspirated through the through-opening 2 of the shield 1 in the direction of the mixing cylinder 20.

Subsequently, the monomer liquid can be aspirated through the sieve element 4. In this respect, the sieve element 4 advantageously has mesh size of less than 30 µm. Due to this small mesh size of the sieve element 4, the flow rate of the monomer is reduced. In order to still achieve homogeneous passage of the liquid of the monomer into the mixing cylinder 20, the size of the sieving area 4 must be adapted accordingly. The ratio of the area 5 of the through-opening 2 to the area 8 of the sieve element 4 thus also determines the volume of a monomer liquid that is aspirated into the mixing cylinder 20 in a unit of time. Accordingly, the use, according to the invention, of the sieve element 4 ensures homogeneous ingress of monomer into the mixing cylinder 20 and simultaneously prevents clogging of the conveyor 122 by bone cement powder.

Figure 3:
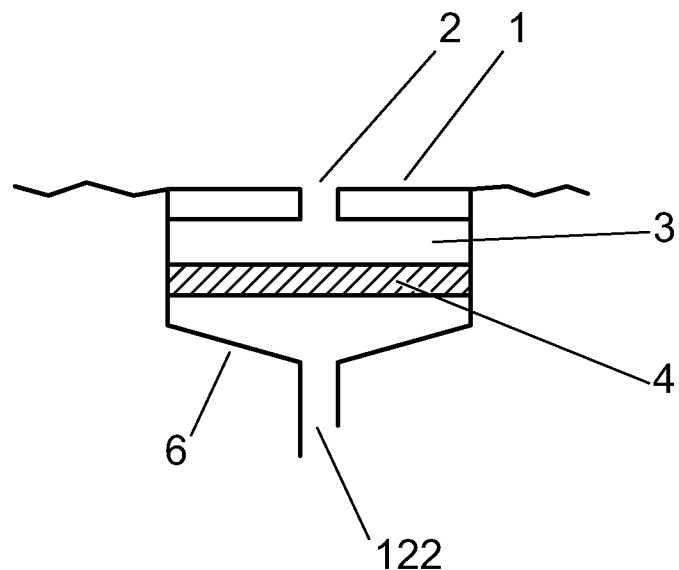
FIG. 3 is a schematic sectional view of a dispensing opening of the mixing facility.

FIG. 3 shows another detail magnification of the intervening space 3 with the integrated sieve element 4 that serves to preventingress of the bone cement powder from the mixing cylinder 20 through the through-opening 3 into the conveyor 122. The intervening space 3 has a V-shaped base 6 that has the effect of a nozzle on the monomer flowing from the conveyor 122. The sieve element 4 is arranged above the dispensing opening of the conveyor 122. The sieve element can be a punched, woven or knitted structure that is composed of metals, plastic materials and/or combinations thereof.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A bone cement system (100) comprising a mixing facility (10) for mixing and dispensing of bone cement, a reservoir container (112) for a monomer, and a conveyor (122), wherein
   the mixing facility (10) comprises a mixing cylinder (20);
   the mixing cylinder (20) stores a bone cement powder;
   the conveyor (122) conveys the monomer from the reservoir container (112) into the mixing cylinder (20);
   a sieve element (4) is arranged between the reservoir container (112) and the mixing facility (10) to prevent ingress of the bone cement powder from the mixing cylinder (20) into the conveyor (122), the sieve element (4) having a mesh size between 5 µm and 30 µm;
   the mixing facility (10) comprises a dispensing opening (23) for dispensing the bone cement mixed from the bone cement powder and the monomer;
   the dispensing opening (23) comprises a shield (1) having at least one through-opening (2); and
   a ratio of an area of the through-opening (2) to the area of the sieve element (4) is at most 1 to 3, and a distance between the shield (1) and the sieve element (4) is between 1 mm and 10 mm.

2. The bone cement system (100) according to claim 1, wherein the sieve element (4) is stored in an intervening space (3) connectable to the dispensing opening (23) of the mixing facility (10), and the conveyor (122) ends in the intervening space.

3. The bone cement system (100) according to claim 1, wherein the sieve element (4) has a mesh size between 5 µm and 25 µm.

4. The bone cement system (100) according to claim 1, wherein the ratio of the area of the through-opening (2) to the area of the sieve element (4) is between 1 to 4 and 1 to 20.

5. The bone cement system (100) according to claim 1, wherein the distance between the shield (1) and the sieve element (4) is between 2 mm and 10 mm.

6. The bone cement system (100) according to claim 1, wherein the through-opening (2) has a shape selected from circular, oval, star-shaped, and slit-shaped.

7. The bone cement system (100) according to claim 1, wherein the shield (1) extends from the through-opening (2) in a funnel shape.

8. The bone cement system (100) according to claim 1, wherein a mixing plunger (21) is arranged in the mixing cylinder (20), and where the mixing plunger (21) is axially movable by an actuation rod (50) guided to exit in a sealed manner at a first cylinder end (30).

9. The bone cement system (100) according to claim 1, wherein a plunger system (40) is axially pushable into the mixing cylinder (20) to dispense through the dispensing opening (23) a bone cement mixed from the bone cement powder and the monomer.

10. The bone cement system (100) according to claim 1, further comprising a reservoir facility (110) having a valve (115) to control and/or trigger an outflow of the monomer from the reservoir container (112).

11. The bone cement system (100) according to claim 1, further comprising a base (120), wherein the base (120) stores the mixing facility (10) and the reservoir container (112).

\* \* \* \* \*